United States Patent [19]
O'Neil et al.

[11] Patent Number: 6,071,311
[45] Date of Patent: Jun. 6, 2000

[54] CYLINDRICAL BOX FEMORAL STEM

[75] Inventors: Michael O'Neil, West Barnstable; Arnold Oyola, Taunton, both of Mass.

[73] Assignee: Johnson & Johnson Professional, Inc., Raynham, Mass.

[21] Appl. No.: 09/134,656

[22] Filed: Aug. 14, 1998

[51] Int. Cl.[7] ...................................................... A61F 2/38
[52] U.S. Cl. .............................................. 623/20; 623/18
[58] Field of Search ................................... 623/18, 20, 23

[56] References Cited

U.S. PATENT DOCUMENTS

| | | | |
|---|---|---|---|
| 4,219,893 | 9/1980 | Noiles | 3/1.911 |
| 4,301,553 | 11/1981 | Noiles | 3/1.911 |
| 4,404,691 | 9/1983 | Buning et al. | 3/1.911 |
| 4,578,081 | 3/1986 | Harder et al. | 623/22 |
| 4,624,673 | 11/1986 | Meyer | 623/16 |
| 4,714,471 | 12/1987 | Grundei | 623/20 |
| 4,790,852 | 12/1988 | Noiles | 623/18 |
| 4,790,854 | 12/1988 | Harder et al. | 623/20 |
| 4,822,366 | 4/1989 | Bolesky | 623/20 |
| 4,834,758 | 5/1989 | Lane et al. | 623/18 |
| 4,846,839 | 7/1989 | Noiles | 623/18 |
| 4,888,021 | 12/1989 | Forte et al. | 623/20 |
| 4,904,110 | 2/1990 | Klein | 403/379 |
| 4,936,853 | 6/1990 | Fabian et al. | 623/20 |
| 4,944,757 | 7/1990 | Martinez et al. | 623/20 |
| 4,985,037 | 1/1991 | Petersen | 623/20 |
| 5,011,496 | 4/1991 | Forte et al. | 623/20 |
| 5,019,103 | 5/1991 | Van Zile et al. | 623/20 |
| 5,057,111 | 10/1991 | Park | 606/69 |
| 5,127,914 | 7/1992 | Calderale et al. | 606/65 |
| 5,133,760 | 7/1992 | Petersen et al. | 623/20 |
| 5,137,535 | 8/1992 | Keller | 623/20 |
| 5,152,796 | 10/1992 | Slamin | 623/20 |
| 5,194,066 | 3/1993 | Van Zile | 623/20 |
| 5,258,032 | 11/1993 | Bertin | 623/20 |
| 5,269,784 | 12/1993 | Mast | 606/69 |
| 5,290,313 | 3/1994 | Heldreth | 623/20 |
| 5,326,359 | 7/1994 | Oudard | 623/20 |
| 5,330,534 | 7/1994 | Herrington et al. | 623/20 |
| 5,336,225 | 8/1994 | Zang | 606/73 |
| 5,370,701 | 12/1994 | Finn | 623/20 |
| 5,397,360 | 3/1995 | Cohen et al. | 623/16 |
| 5,405,395 | 4/1995 | Coates | 623/20 |
| 5,413,605 | 5/1995 | Ashby et al. | 623/20 |
| 5,556,433 | 9/1996 | Gabriel et al. | 623/20 |
| 5,609,641 | 3/1997 | Johnson et al. | 623/20 |
| 5,683,469 | 11/1997 | Johnson et al. | 623/20 |
| 5,702,460 | 12/1997 | Carls et al. | 623/20 |
| 5,766,255 | 6/1998 | Slamin et al. | 623/20 |
| 5,879,391 | 3/1999 | Slamin | 623/20 |
| 5,944,756 | 8/1999 | Fischetti et al. | 623/18 |

FOREIGN PATENT DOCUMENTS

| | | |
|---|---|---|
| 0144667 | 6/1985 | European Pat. Off. . |
| 0307655 | 3/1989 | European Pat. Off. .......... A61F 2/38 |
| 0529408 | 3/1993 | European Pat. Off. .......... A61F 2/38 |
| 0531263 | 3/1993 | European Pat. Off. .......... A61F 2/38 |
| 0621019 | 10/1994 | European Pat. Off. . |
| 1575278 | 9/1980 | United Kingdom .............. A61F 1/03 |
| 2259253 | 3/1993 | United Kingdom .............. A61F 2/02 |
| 9709939 | 3/1997 | WIPO . |

OTHER PUBLICATIONS

Johnson & Johnson Orthopaedics Research & Development "*P.F.C.® Modular Knee System Research Data and Laboratory Testing,*" cover and pp. 8, 36 and 37 (1989).

*Primary Examiner*—David H. Willse
*Assistant Examiner*—Suzette J. Jackson
*Attorney, Agent, or Firm*—Nutter, McGlennen & Fish, LLP

[57] ABSTRACT

The present invention provides a femoral component of a modular knee prosthesis having a first condylar portion, a second condylar portion and a box structure having a radiused superior surface, an inferior surface, and an aperture extending therebetween. The box structure may be modular to accommodate varying femoral geometries. Pairs of opposing surface features, such as grooves, are formed on the box structure and allow for anterior-posterior positioning of a stem component such as a femoral stem, sleeve or sleeve adapter. Additional surface features may be provided to centrally locate the stem component.

21 Claims, 8 Drawing Sheets

CYLINDRICAL BOX FEMORAL STEM

CROSS-REFERENCE TO RELATED APPLICATIONS

Not applicable

STATEMENT REGARDING FEDERALLY SPONSORED RESEARCH

Not applicable

FIELD OF THE INVENTION

The invention relates to medical devices, and more particularly to prosthetic joint components.

BACKGROUND OF THE INVENTION

Joint arthroplasty is a well-known surgical procedure by which a diseased and/or damaged natural joint is replaced by a prosthetic joint. A typical knee prosthesis includes a tibial component, a femoral component, a femoral stem assembly, and a patellar component. The femoral component generally includes a pair of spaced apart condylar portions, the superior surfaces of which articulate with a portion of the tibial component. The femoral stem assembly provides lateral stability, and it typically includes a member that is inserted within a reamed intramedullary canal at the distal end of a femur. The stem is typically coupled to the femoral component by a collar and bolt.

Although modular systems can provide an advantageous reduction in joint component inventory, known systems do not fully address the problems associated with variations in intramedullary canal geometry. Specifically, the variations in the morphology of the intermedullary canal often do not match the geometry of the stem, forcing the surgical positioning of the femoral component that is mated to the stem to be determined by considerations other than the shape of the canal.

For example, if the implant geometry does not match the canal geometry, the stem of the implant can contact the cortical wall of the intramedullary canal while the stem is being impacted. This problem can be further complicated when a femoral stem is mated to a sleeve that increases the effective length of the stem so that it is in a bowed portion of the intramedullary canal.

In response to the above problems, a surgeon may be forced to remove the stem (or entire component) and replace it with a stem having a smaller diameter or shorter length, even if the replacement stem is thought to be less suitable than the original stem, but for the improper fit. Also, the surgeon may have to cut notches in the femur to accommodate a shifted femoral component.

Therefore, despite the existence of joint prostheses having modular components, there remains a need for a modular joint prosthesis that has greater versatility to accommodate differing patient anatomy and joint conditions.

BRIEF SUMMARY OF THE INVENTION

The present invention relates to a modular knee joint prosthesis having improved versatility while reducing overall component piece count. Components of the modular prosthesis of the invention are able to be used with both right and left side prostheses.

The present invention provides a modular knee prosthesis which includes a femoral component having a first condylar portion, a second condylar portion, and a box structure having a radiused superior surface. The prosthesis may also include a femoral stem, a sleeve and/or a sleeve adapter component which is secured to the box structure by a bolt member.

Pairs of opposing surface features, such as grooves, are formed on the radiused box structure and allow for anterior-posterior positioning of a stem component such as a femoral stem, sleeve or sleeve adapter. Additional surface features may be provided to centrally locate the stem component on the prosthesis. In another embodiment, the radiused box structure is modular so as to accommodate varying femoral geometries.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF THE INVENTION

Figure 1:
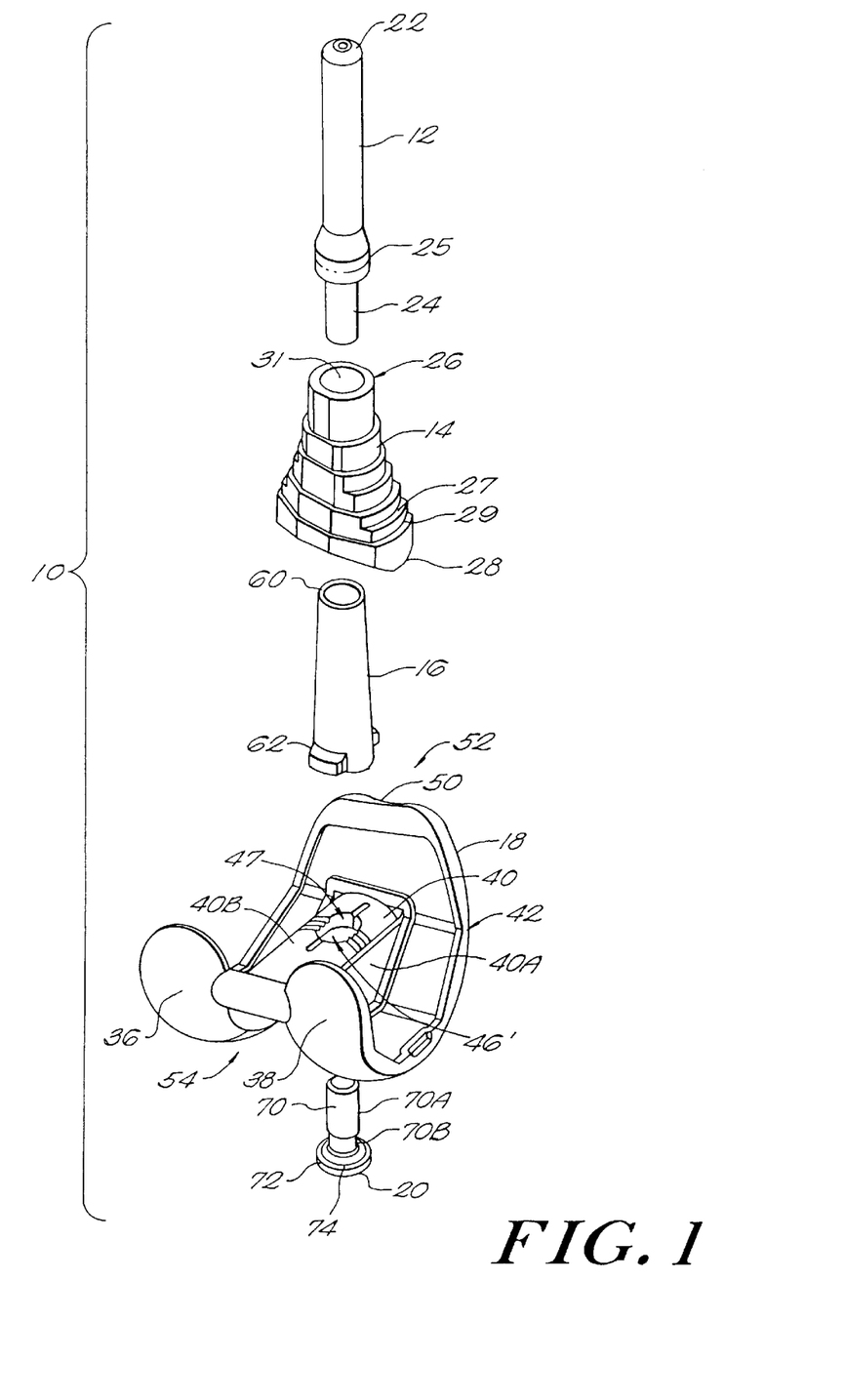
FIG. 1 is an exploded view of a multi-piece prosthetic joint component.

FIG. 1 is an exploded view of a modular prosthetic joint prosthesis 10 that includes a stem 12, a sleeve member 14, a sleeve adapter or post 16, a femoral component 18 having a curved seating or mounting surface, and a bolt member 20. The construction of the present invention provides a plurality of mounting possibilities that are compatible with the various possible orientations of the femoral stem when mounted within the distal portion of the femur.

The stem 12 includes a proximal end 22 and a distal end 24 which includes an engaging shoulder portion 25 adapted for mating with a proximal end 26 of sleeve 14. The distal end 24 may have threads formed thereon effective to engage a threaded portion of sleeve adapter 16, as discussed in more detail later herein. The sleeve 14 includes proximal and distal ends 26, 28 with an outer surface 27 extending therebetween. The outer surface 27 may be irregularly shaped, so as to include, for example, steps 29. The proximal portion 26 of the outer surface 27 may have a diameter substantially smaller than the diameter as measured at the distal end 28. Preferably, the diameter of the proximal end 26 of sleeve 14 is less than the outer diameter of the femoral stem shoulder portion 25. The sleeve 14 also includes a bore 31 extending therethrough from the proximal end 26 to the distal end 28.

The distal end 28 of femoral sleeve 14 is further adapted for mating with sleeve adapter 16 which has a Morse taper. The sleeve adapter 16 includes a proximal end 60 and a distal end 62 which is mateable to the femoral component 18 shown in FIGS. 2A–2B. As shown in FIGS. 3A–3C, the distal end 62 includes a distally facing surface 63 having a complementary medially-laterally extending radius for mating with the radiused seating surface 40B of femoral component 18 as discussed in further detail herein.

The proximal end 60 of stem adapter 16 defines a first cavity 61 for receiving the distal end portion 24 of the sleeve 12. The illustrated adapter 16 has a second cavity 63 that receives bolt member 20 when the components of the prosthesis are assembled as discussed in further detail herein. Both cavities 61, 63 may have threads formed therein for threadably engaging stem 12 and bolt member 26, respectively. In other embodiments of the invention, the Morse taper is directly matable with a femoral stem or other component without a femoral sleeve.

Figure 2A:
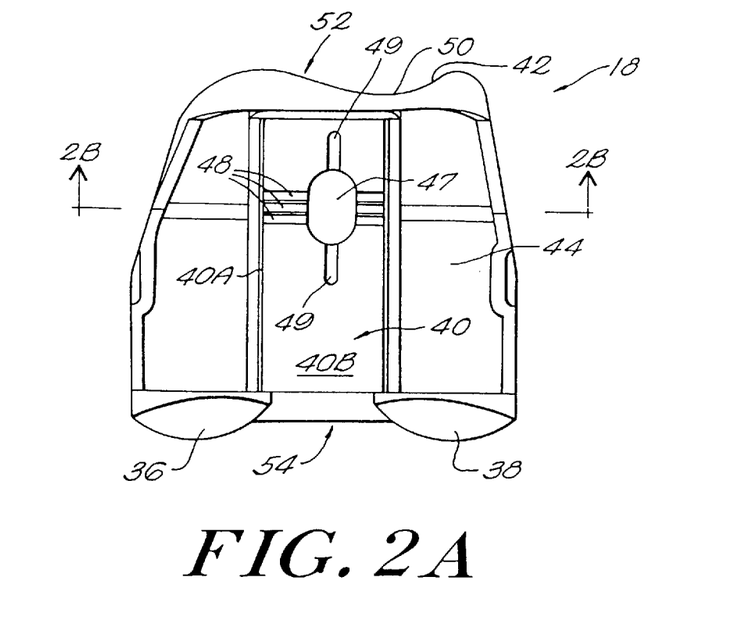
FIG. 2A is a top view of the femoral component shown in FIG. 1.
Figure 2B:
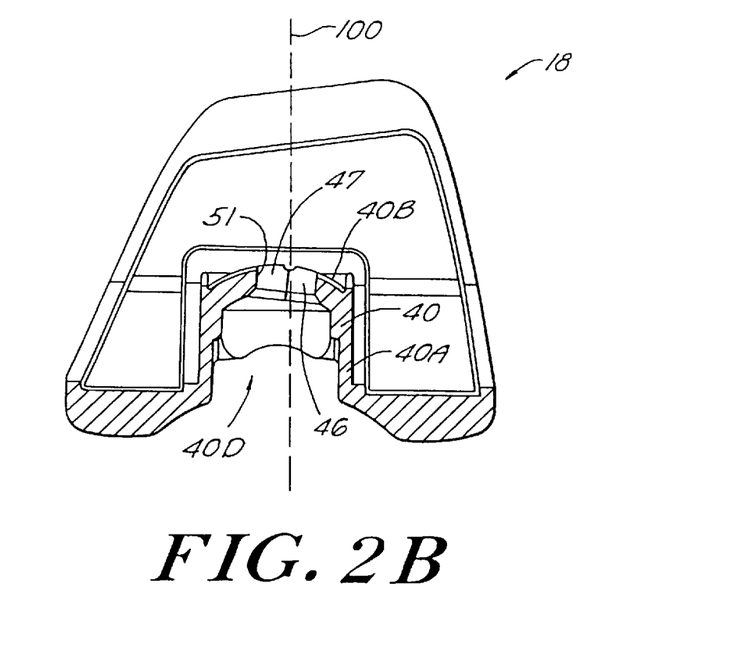
FIG. 2B is a sectional view of the femoral component of FIG. 2A, taken along line 2B—2B.
Figure 3A:
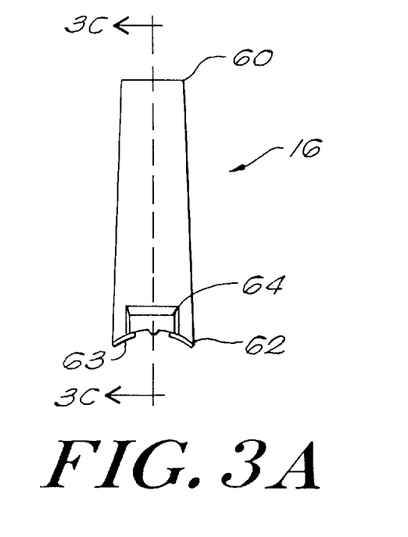
FIG. 3A is a front view of the sleeve adapter shown in FIG. 1.
Figure 3B:
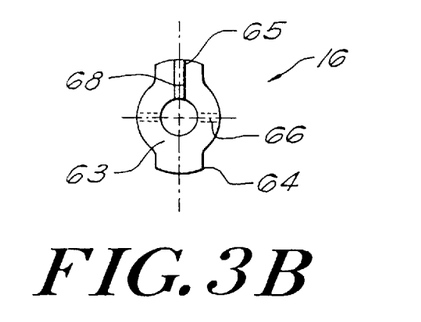
FIG. 3B is a bottom view of the sleeve adapter shown in FIG. 3A.
Figure 3C:
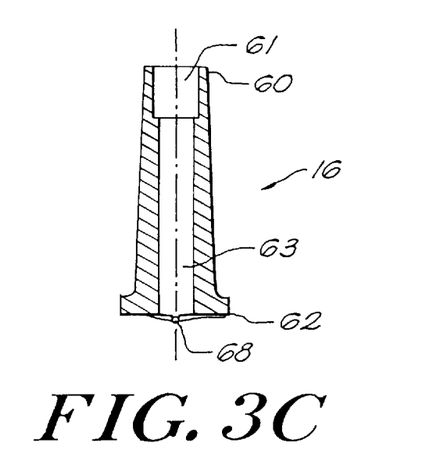
FIG. 3C is a sectional view of the sleeve adapter illustrated taken along line 3C—3C in FIG. 3A.

Referring to FIGS. 1 through 2B, the femoral component 18 has a pair of condylar portions 36, 38 that are connected by an intercondylar boss or box structure 40. The femoral component 18 has an articulation surface 42 and an opposed surface 44. Further, the femoral component 18 has an anterior side 52 and a posterior side 54. The anterior side 52 of the femoral component 18 includes a patellar groove 50, shown in FIG. 2A, within which seats a patellar prosthetic component (not shown). The surfaces 42 of the curved condylar portions 36, 38 articulate with a prosthetic tibial component (not shown) mounted on the head of the tibia, in a manner well known to those of ordinary skill in the art.

The boss structure 40 has a pair of substantially vertical side walls 40A that are connected by a top or superior, radiused seating surface 40B. The boss structure 40 further has a cavity 46 formed within a bottom or inferior surface 40D. An aperture 47 defined by the boss structure 40 extends between the surfaces 40B, 40D, respectively, of the boss structure 40 and has a selected shape such that it can be elongated in the anterior-posterior direction or alternatively, in the medial-lateral direction. The shape of the aperture 47 in the boss structure 40 can be elliptical, oval, spherical, or of any other suitable shape that allows a sufficient amount of translation of the securing bolt shaft when the bolt is mounted within the aperture.

The cavity 46 is further defined by inclined sidewalls 51 which are canted with respect to a central vertical axis 100 which is co-axial with vertical sidewalls 40A. The sidewalls 51 may be angled in the range of 0 to 30 degrees with respect to vertical axis 100. Once the prosthesis is assembled, the sidewalls 51 engage bolt member 20 so that an upper portion 70A of bolt member extends from aperture 47 at a desired angulation. Typically, the sidewalls will be angled to seat bolt member 20 to match the desired valgus angle of the specific patient. The valgus angle is the angle between the center line of the femur and an imaginary vertical line extending from the distal femur to the center of the femoral head. This angle is generally in the range of 5 to 9 degrees.

As shown in FIGS. 1 and 2A, seating surface 40B of boss structure 40 has formed thereon at least one pair of opposed surface features or grooves 48 that are elongated in the medial-lateral direction. The seating surface 40B further includes another set of at least one pair of opposed surface features or grooves 49 that extend in the anterior-posterior direction. The grooves 48, 49 are effective to engage corresponding surface features on another femoral component such as a stem, sleeve, and stem adapter, as discussed in more detail herein.

Referring now to FIG. 2B, the femoral component 18 is shown in cross-section and the curvature or radius of seating surface 40B is clearly visible. In an exemplary embodiment, the radius is in the range of about 2 mm to 40 mm over an approximately 90° segment of arc. Varying the curvature of seating surface 40B of boss structure 40 provides the flexibility to change the angulations of another prosthesis component such as a femoral stem, sleeve and/or sleeve adapter. By varying the curvature of the seating surface, the angulation of the femoral stem, sleeve, and/or adapter component can be correspondingly varied in the range of 0° to 45° degrees in either direction.

Referring to FIGS. 2A–3C, the seating surface 40B of boss structure 40 has formed thereon a first set positioning elements or surface features 48, e.g. grooves or protrusions that preferably extend in the medial lateral direction and are spaced in the anterior-posterior direction. The surface features 48 of the boss structure 40 cooperate with another complementary surface feature 66 formed on the distal end of the sleeve adapter 16 or directly on the femoral stem itself, to position the stem 12 at one of the mounting positions described further below. The surface features 48 of boss structure 40 can be in the form of an indentation or a raised structure, such that surface features 48, 66 are complementary. Thus if surface features 48 are in the form of grooves, surface features 66 will be in the form of a protrusion dimensioned to fit within the grooves.

The surface features or grooves allow the positioning of the stem in a range of positions in the Anterior-Posterior direction. For example, if it is desirable to locate the femoral stem anteriorly, the adapter 16 can be positioned and mounted within the anterior-most groove. Similarly, if it is desirable to mount the stem posteriorly, the adapter 16 can be mounted within the posterior-most groove. Although the femoral component of the drawings includes three pairs of opposed grooves, those of ordinary skill in the art will recognize that any number of grooves can be formed in the top boss surface.

The top surface 40B of boss structure 40 also has formed thereon a second set of positioning elements or surface features 49, e.g. grooves or protrusions that preferably extend in the anterior-posterior direction. The surface features 49 of the boss structure 40 cooperate with another complementary surface feature 68 formed on the distal end of the sleeve adapter 16 or directly on the femoral stem itself, to position the stem 12 at the proper orientation. It is understood that surface features 49, 68 are intended to be complementary. Preferably, the surface features 49 are located centrally relative to aperture 47 or at the mid-point between opposing medial-lateral surface features 48 to position the stem 12 at a proper position on the prosthesis. Once positioned properly, the components are secured together by bolt member 20.

FIG. 1 illustrates a preferred embodiment of the securing bolt 20 of the present invention. The bolt 20 of a first embodiment has a shaft portion 70 that extends upwardly and outwardly from a bolt head 72. The shaft has an upper portion 70A which may have threads formed thereon. The upper portion 70A preferably has an outer diameter less than the outer diameter of bolt head 72. An indented neck portion 70B separates the upper 70A from the bolt head 72 of bolt 20. The outer diameter of the upper portion 70A is preferably more than the outer diameter of the lower neck portion 70B. The bolt head portion 72 has included a boss aperture-engaging surface 74. The mating engagement of the aperture-engaging surface 74 of the bolt head 72 and the boss cavity 46 positions the bolt shaft within the aperture 47.

FIGS. 4–8B illustrate a prosthesis system 11 which is a variation of system described in FIGS. 1–3C. System 11 includes the various components present in FIG. 1, including a first prosthesis component, such as a stem 12, a sleeve 14 and a sleeve adapter 16. System 11 also includes an additional modular box component 78 having a radiused seating surface 88. As used herein, the term "box structure" refers to a component having an integrally formed radiused surface as illustrated in FIGS. 1–3C and also a modular component having a removable structure with a radiused surface as illustrated in FIGS. 4–8B.

A femoral component 18' and a bolt member 20' are also provided which differ slightly from the components described above with respect to FIGS. 1–3C. In this embodiment, the modular box component 78 allows for the interchanging of box components having varied curvatures or radiuses to provide a variety of mounting possibilities for the prosthesis.

Figure 4:
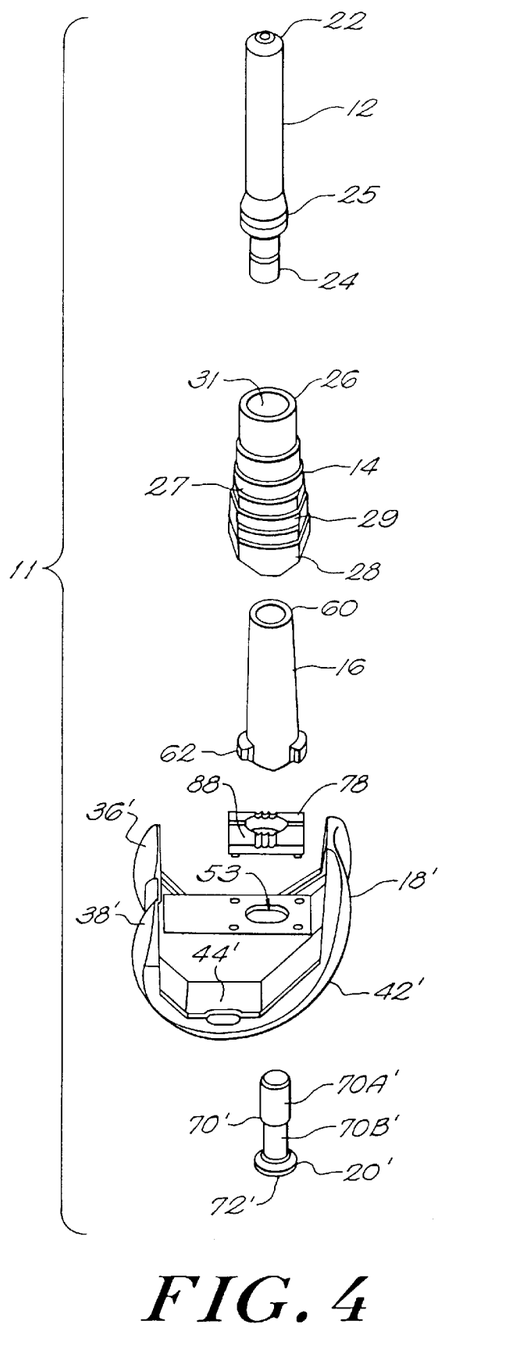
FIG. 4 is an exploded view of an alternative embodiment of the multi-piece prosthetic joint component shown in FIG. 1.
Figure 5A:
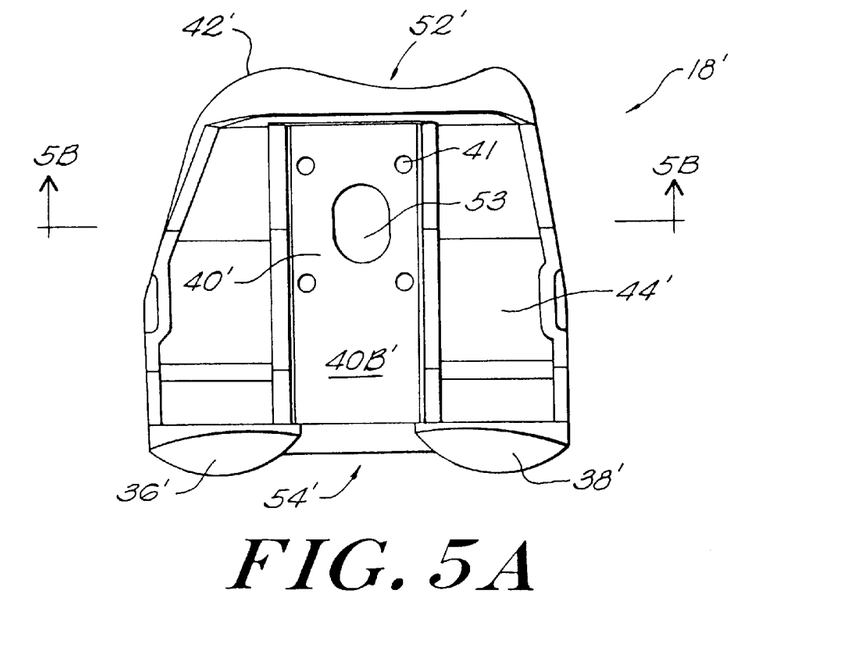
FIG. 5A is a top view of the femoral component shown in FIG. 4.
Figure 5B:
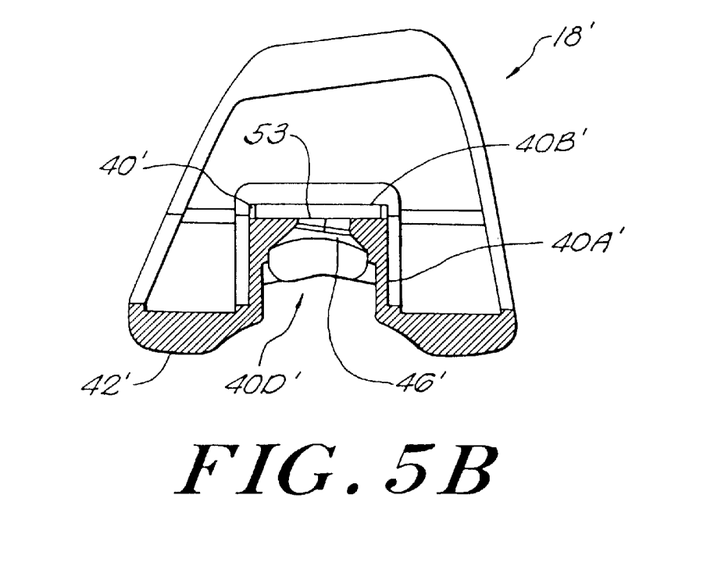
FIG. 5B is a sectional view of the femoral component illustrated taken along line 5B—5B in FIG. 5A.

Referring to FIGS. 4–5B, the femoral component 18' has a pair of condylar portions 36', 38' that are connected by an intercondylar region or boss structure 40'. The femoral component 18' has an articulation surface 42' and an opposed surface 44'. Further, the femoral component 18' also has an anterior side 52' and a posterior side 54'.

The boss structure 40' has a pair of substantially vertical side walls 40A' that are generally orthogonal to a top superior surface 40B'. The top surface 40B' is substantially horizontally oriented and extends in the transverse plane. The transverse plane is defined as the horizontal plane that extends through the knee of an upright subject that is orthogonal to both the coronal plane and the sagittal plane as will be appreciated by those having ordinary skill in the art.

The top surface 40B' has formed thereon a plurality of mounting apertures 41 effective to engage the modular box component 78, as discussed in more detail later herein. The boss 40' further has a cavity 46' formed within a bottom inferior surface 40D'. An aperture 53 defined by the cavity 46' extends between surfaces 40B', 40D', respectively, of the boss structure 40' and has a selected shape such that it can be elongated in the anterior-posterior direction or alternatively, in the medial-lateral direction. As illustrated, the top surface 40B' is configured to engage modular box component 78.

Figure 6A:
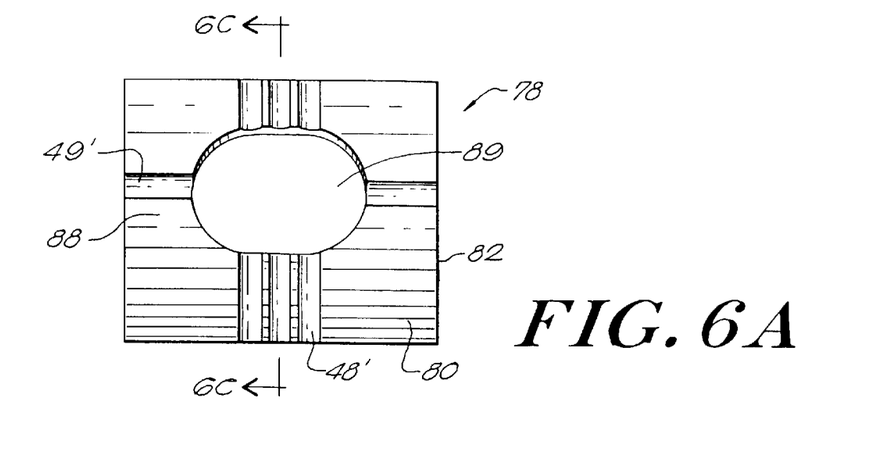
FIG. 6A is a top view of the box component shown in FIG. 4.
Figure 6B:
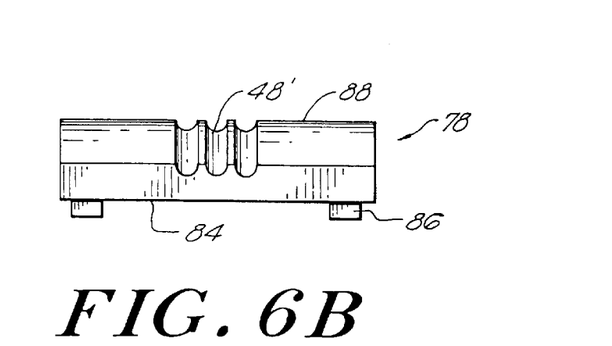
FIG. 6B is a side view of the box component shown in FIG. 6A.
Figure 6C:
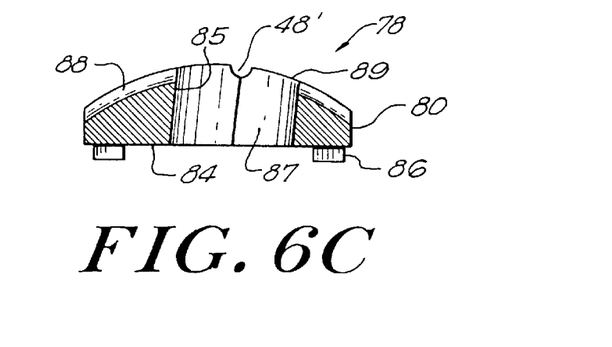
FIG. 6C is a sectional view of the box component illustrated in FIG. 6A, taken along line 6C—6C.
Figure 7A:
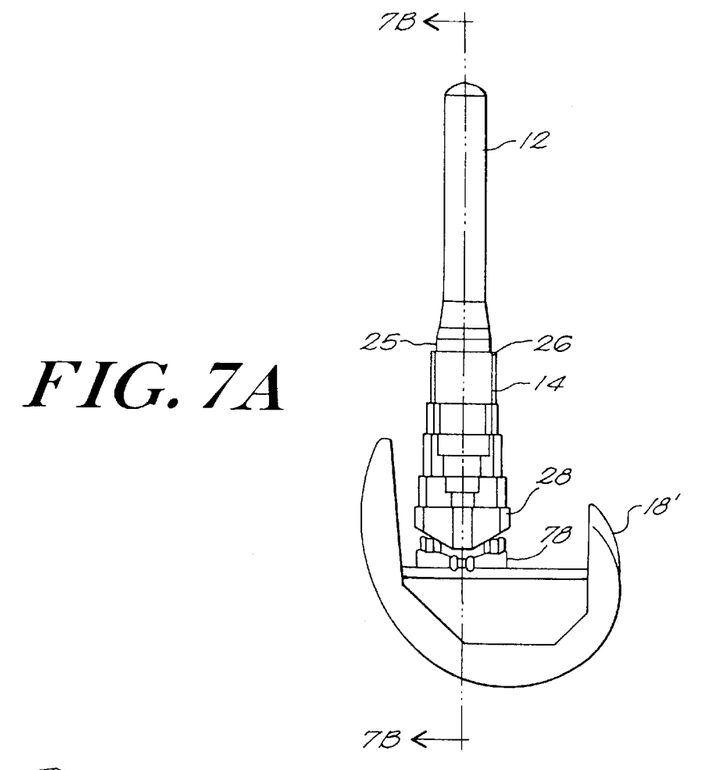
FIG. 7A is a side elevational view of the assembled joint component shown in FIG. 4.
Figure 7B:
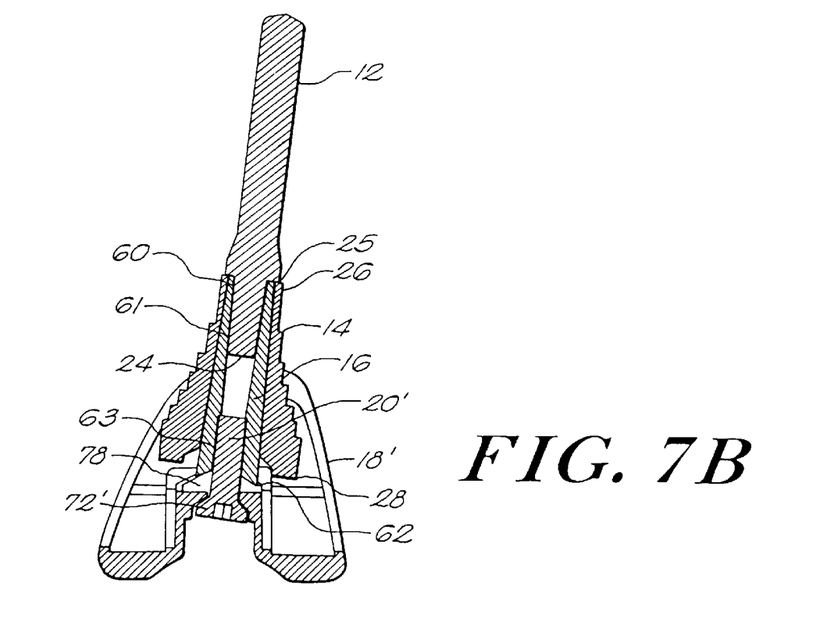
FIG. 7B is a sectional view of the joint component of FIG. 7A taken along line 7B—7B.

With reference to FIGS. 6A–6C, the modular box component 78 has a central body portion 80 that has an outer peripheral surface 82 and a boss engaging surface 84 which includes surface protrusions or mounting feet 86. The box component 78 further includes a radiused seating surface 88 mateable with a complementary surface on another component, such as a femoral stem, sleeve or sleeve adapter. Seating surface 88 also has formed thereon a superior aperture 89 which has a selected shape such that it can be elongated in the anterior-posterior direction or alternatively, in the medial-lateral direction. In this embodiment, the seating surface 88 is substantially identical to seating surface 40B' as discussed with reference to FIGS. 1–2B. However, the modular construction of the box component 78 illustrated in FIGS. 4 and 6A–6C allows the interchanging of box components having different curvatures or radiuses to accommodate differing patient anatomies.

Mounting feet 86 are adapted to engage the mounting apertures 41 formed on the top surface 40B' of boss structure 40' such that apertures 53 and 89 are aligned. The mating engagement between the feet 86 and the apertures 41 prevents unwanted movement and/or rotation of the box component 78 when the box component 78 is mounted on the top surface 40B' of boss structure 40'.

The box component 78 further has a through-bore 87 which extends between surfaces 84, 88, respectively, of the box component 78. The through-bore 87 is further defined by inclined sidewalls 85 which are angled to match a desired valgus angle to seat bolt member 20' in the desired orientation. The bolt member 20' for use with the embodiment shown in FIG. 4 has a shaft portion 70' which includes threaded portion 70A' and a neck portion 70B' extending from a bolt head 72'.

In an exemplary embodiment, the aperture 89 is not at the center of the box component 78, but is offset toward one of the substantially flat sides 82. Thus, in cooperation with the radiused seating surface 88, offset of the femoral stem 12 can be achieved in any number of different orientations simply by placing the aperture 89 either closer or farther to one of the flat sides 82 and relocating the alignment guides 48' and 49' appropriately.

Referring to FIGS. 7A–8B, an exemplary modular knee prosthesis as shown in FIG. 4 can be assembled in the following manner. The following procedure is applicable to both embodiments shown and described herein except for the attachment of a separate box component with respect to the embodiment shown in FIGS. 4–6C. The stem 12 is mated to the sleeve 14 by positioning the mating surface or shoulder 25 upon the proximal end 26 of the sleeve 14. The distal end 24 of stem 12 is passed into the adapter cavity 31 such that the mating surface 25 abuts the proximal end 26 of sleeve 14. The proximal end 60 of adapter 16 is extended into the distal end 28 of sleeve 14. The proximal end cavity 61 of adapter 16 mates with and engages the distal end 24 of stem 12. The box component is then mounted on the top surface 40B', of the boss 40' by aligning and engaging mounting feet 86 with apertures 41.

Figures 8A, 8B:
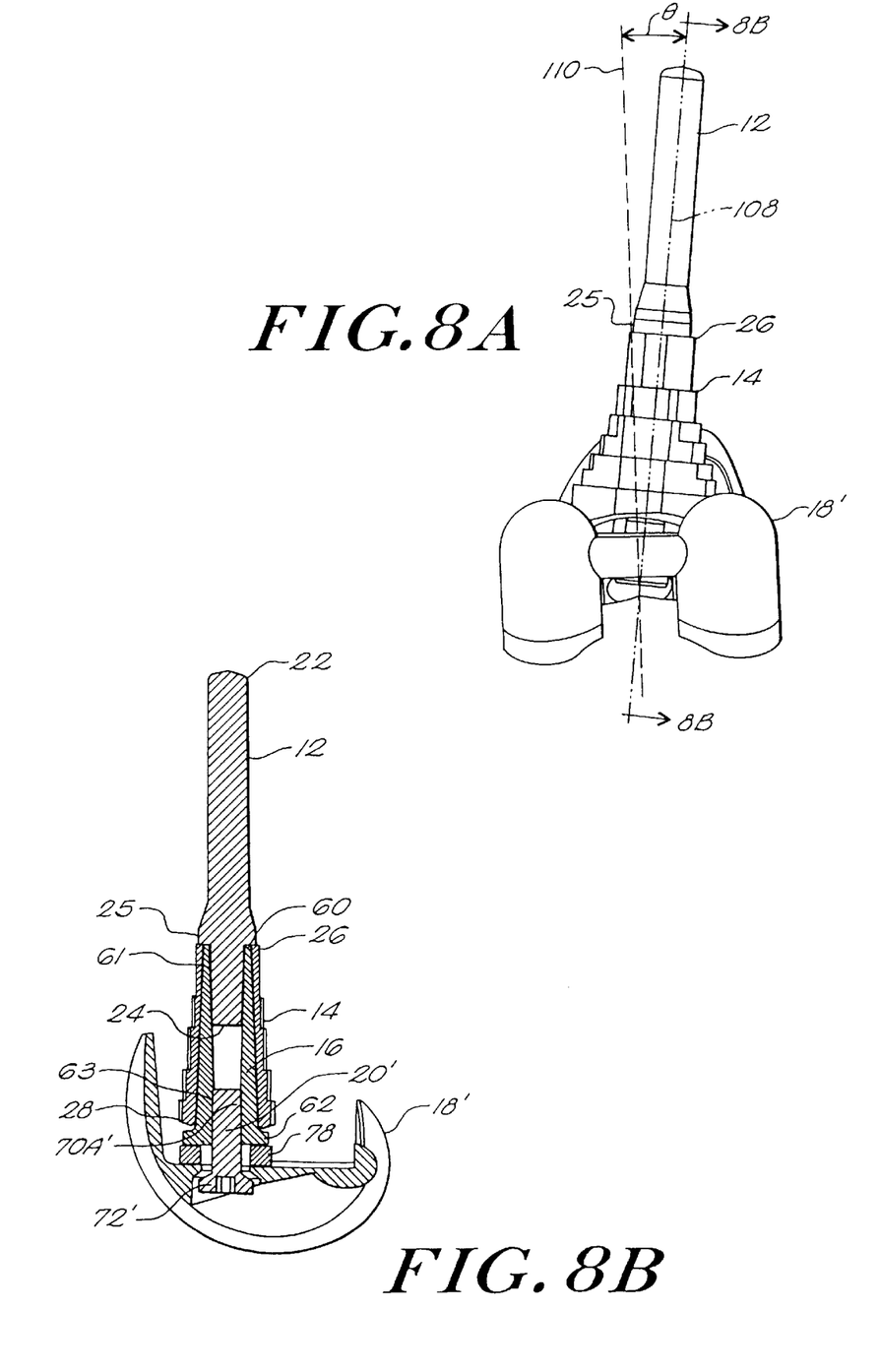
FIG. 8A is a front elevational view of the joint component shown in FIGS. 7A and 7B.
FIG. 8B is a sectional view of the multi-piece prosthetic joint component of FIG. 8A taken along line 8B—8B.

The securing bolt 20' is inserted into the boss cavity 46' from the underside of the boss structure and through the boss aperture 53, such that the bolt shaft extends upwardly from the boss surface. The engaging surface 74' of the bolt head 72' mates with and engages the boss cavity such that the bolt shaft extends through apertures 53. In the embodiment shown in FIG. 4, the bolt shaft will further extend into and through box component 78. Bolt shaft portion 70A' will then engage cavity 63 formed in the distal end 62 of sleeve adapter 16 to secure the component together. As shown in FIG. 8A, in this assembled condition, a longitudinal axis 108 of stem 12 forms an angle θ, the valgus angle, with a vertical axis 110.

In such a configuration, the bolt member is effective to bind the femoral stem to the femoral component by engaging the sleeve adapter. In this axially successive assemblage, the box component of the embodiment of FIG. 4 is held by a threadable engagement or alternatively by an interference-type fit between the sleeve adapter and femoral component by the engagement of the bolt and sleeve adapter.

A variety of modifications and variations of the present invention are possible in light of the above teachings. It is understood that the basic femoral component construction in the present system can be used for either the right or left knee. All references cited herein are expressly incorporated by reference in their entirety.

What is claimed is:

1. A femoral component of a modular knee prosthesis comprising:
   a first condylar portion;
   a second condylar portion; and
   a box structure having a convex superior surface, an inferior surface, and an aperture extending therebetween.

2. The femoral component of claim 1, wherein the aperture is elongate.

3. The femoral component of claim 2, wherein the elongate aperture is oval.

4. The femoral component of claim 3, wherein the elongate aperture extends in an anterior/posterior orientation.

5. The femoral component of claim 4, wherein the elongate aperture is bordered by positioning elements.

6. The femoral component of claim 5, wherein the positioning elements comprise opposing pairs of surface features elongated in a medial-lateral direction and spaced apart in an anterior-posterior direction.

7. The femoral component of claim 6, wherein each pair of surface features defines one of a plurality of anterior-posterior mounting positions.

8. The femoral component of claim 1, wherein the box structure further includes substantially parallel sidewalls which further define the box aperture.

9. The femoral component of claim 8, wherein the parallel sidewalls range from vertical to angled with respect to a vertical axis extending through the femoral component.

10. The femoral component of claim 9, wherein the sidewalls are angled to match a desired valgus angle of a femur.

11. The femoral component of claim 1, wherein the convex surface is integral with the box structure.

12. The femoral component of claim 1, wherein the box structure is modular and includes a box component having a convex superior surface, the box component being mountable upon a substantially horizontal surface which connects the first and second condylar portions.

13. The femoral component of claim 1, further comprising a component having a proximal end and a distal end having a surface effective to mate with the superior surface of the box.

14. The femoral component of claim 13, wherein the distal end surface includes complementary concave surface features adapted to mate with positioning elements formed on the box structure.

15. The femoral component of claim 11, wherein the component is one of a sleeve, a sleeve adapter, and a stem.

16. A modular knee prosthesis comprising:
   a femoral component having a pair of spaced apart condylar portions and a convex boss structure extending between the condylar portions, the boss structure having a boss aperture formed thereon;
   a femoral stem component having a proximal end and a distal end that is mountable to the convex boss structure; and
   a bolt member positionable through the boss aperture so as to secure the femoral stem component to the femoral component.

17. The prosthesis of claim 16, further comprising surface features formed on the convex boss structure which extend in a medial-lateral direction and are spaced apart from one another in an anterior-posterior direction.

18. The prosthesis of claim 17, wherein the surface features comprise grooves which cooperate with complementary protrusions formed on the distal end of the femoral stem component.

19. The prosthesis of claim 16, wherein the boss aperture is elongated in an anterior-posterior direction to allow translation of the bolt member in the anterior-posterior direction.

20. The prosthesis of claim 16, wherein the convex boss structure has a radius of curvature in the range of 2 mm to 40 mm.

21. The prosthesis of claim 16, wherein the distal end of the femoral stem component has a complementary concave surface to mate with the convex boss structure.

* * * * *